United States Patent [19]

Hartwig

[11] Patent Number: 4,731,455
[45] Date of Patent: Mar. 15, 1988

[54] PROCESS FOR THE PREPARATION OF GAMMA-BUTYROLACTAMS

[75] Inventor: Wolfgang Hartwig, Chicago, Ill.

[73] Assignees: Bayer Aktiengesellschaft, Leverkusen, Fed. Rep. of Germany; Chinese Academy of Medical Sciences, Beijing, China

[21] Appl. No.: 914,210

[22] Filed: Oct. 1, 1986

[30] Foreign Application Priority Data

Oct. 18, 1985 [DE] Fed. Rep. of Germany ....... 3537074
Sep. 25, 1986 [DE] Fed. Rep. of Germany ....... 3632589

[51] Int. Cl.$^4$ ............................................ C07D 207/12
[52] U.S. Cl. .................................... 548/544; 548/530;
548/534; 548/539; 548/543; 548/551
[58] Field of Search ......................... 548/544; 564/201

[56] References Cited

FOREIGN PATENT DOCUMENTS 374457 4/1984 Austria .
377982 5/1985 Austria .
0149093 7/1985 European Pat. Off. .
0193887 9/1986 European Pat. Off. .

OTHER PUBLICATIONS

*Planta Medica*, vol. 32, 1977, pp. 81 to 85, Mester et al.
*Phytochemistry*, vol. 17, 1978, pp. 1194 to 1195, Rakosh et al.
*J. Chem. Soc., Chem. Commun.*, (1978), No. 7, pp. 281 to 282, Aboo Shoeb et al.
N. L. Drake and G. B. Cooke, *Organic Syntheses*, vol. 2, pp. 406 to 407, [date not available].
*Methoden Der Organischen Chemie*, (Houben-Weyl), Band IV/1d, 1981, p. 267.
*Methoden Der Organischen Chemie*, (Houben-Weyl), Band VIII, 1952, p. 145.
*Methoden Der Organischen Chemie*, (Houben-Weyl), Band XIII/2a, 1973, pp. 289 to 294, 302 to 312.
*J. Chem. Soc., Chem. Commun.*, (1972), pp. 868 to 869; Brown et al.
International Journal of Methods in Synthetic Organic Chemistry, *Synthesis*, 1981, pp. 1 to 28, Mitsunobu.
International Journal of Methods in Synthetic Organic Chemistry, *Synthesis*, 1980, pp. 297 to 299.
Fieser et al., "Reagents for Organic Synthesis", vol. 6, (1977)—Wiley-Interscience, N.Y., London, pp. 427–428.

*Primary Examiner*—Joseph Paul Brust

*Attorney, Agent, or Firm*—Sprung Horn Kramer & Woods

[57] ABSTRACT

A process for the preparation of a C(3)–C(4)-transconfigurated γ-butyrolactam of the formula (I)

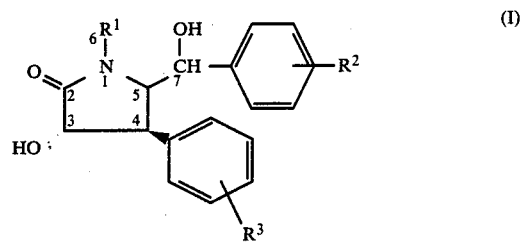

in which
R$^1$ represents hydrogen or alkyl, aryl or aralkyl with in each case up to 10 carbon atoms and
R$^2$ and R$^3$ are identical or different and represent hydrogen, alkyl, aryl, aralkyl, alkoxy, aryloxy or aralkoxy with in each case up to 10 carbon atoms, acyl with up to 18 carbon atoms, trifluoromethyl, trifluoromethoxy, nitro, hydroxyl, halogen, amino, carboxyl, sulpho, dialkylamino with up to 4 carbon atoms in the alkyl groups or acylamino with up to 18 carbon atoms, in the form of their isomers, isomer mixtures, racemates or optical antipodes, comprising oxidizing a compound of the formula (II)

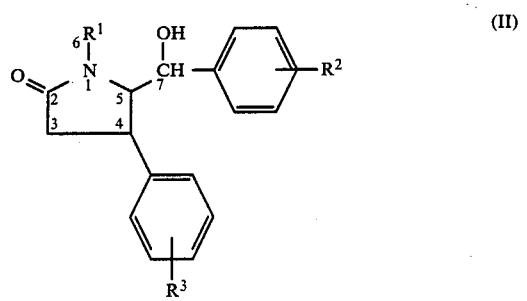

in which
R$^1$, R$^2$ and R$^3$ have the above-mentioned meanings, in an inert organic solvent in the presence of a base. Such γ-butyrolactams have an antiamnesic action.

13 Claims, No Drawings

PROCESS FOR THE PREPARATION OF GAMMA-BUTYROLACTAMS

BACKGROUND OF THE INVENTION

The invention relates to a process for the preparation of γ-butyrolactams, which have a useful antiamnesic action.

It is known that *Rutaceae Clausena anicata* is used as a folk medicine in certain parts of Africa (I. Mester et al., *Planta Medica*, 32, 81 (1977)). It is also known that the crude extract of *Clausena indica* Oliv. has a cardiovascular activity, and that two coumarin derivatives, clausmarin A and B, isolated from *Clausena pentaphalla (Roxb.)* by thin layer chromatography have a spasmolytic activity (Dhan Prakash et al., *Phyochem.*, 17, 1194 (1978); and Aboo Shoeb et al., *J. Chem. Soc., Chem. Commun.*, 1978, 281). The aqueous extract of leaves of *Clausena Lansium (lour) Skeels* is also regarded in Chinese folk medicine as an effective agent which protects the liver and is employed against acute and chronic viral hepatitis. It has been possible to isolate (±)3(S*), 4(R*), 5(R*), 7(S*)-3-hydroxy-5-α-hydroxybenzyl-1-methyl-4-phenylpyrrolidin-2-one (clausenamide) from this extract as one of the main constituents.

Clausenamide and the derivatives prepared from clausenamide show an antiamnesic action and an action affording protection from cerebral hypoxia in animal experiments. Since larger amounts of substance are required for further pharmacological studies, and on the other hand only 1.5 g of starting compound can be obtained from 4 kg of dried leaves by the expensive extraction process, it was necessary to provide a process for chemical synthesis.

SUMMARY OF THE INVENTION

The present invention relates to a process for the preparation of γ-butyrolactams, having a C(3)-C(4)-trans-configuration, of the general formula (I)

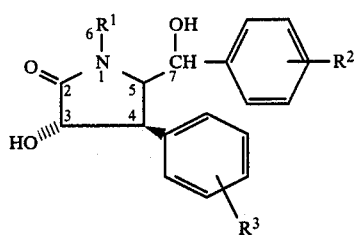

in which
R$^1$ represents hydrogen or alkyl, aryl or aralkyl with in each case up to 10 carbon atoms and
R$^2$ and R$^3$ are identical or different and represent hydrogen, alkyl, aryl, aralkyl, alkoxy, aryloxy or aralkoxy with in each case up to 10 carbon atoms, acyl with up to 18 carbon atoms, trifluoromethyl, trifluoromethoxy, nitro, hydroxyl, halogen, amino, carboxyl, sulpho, dialkylamino with up to 4 carbon atoms in the alkyl groups or acylamino with up to 18 carbon atoms,
in the form of their isomers, isomer mixtures, racemates or optical antipodes, characterised in that compounds of the general formula (II)

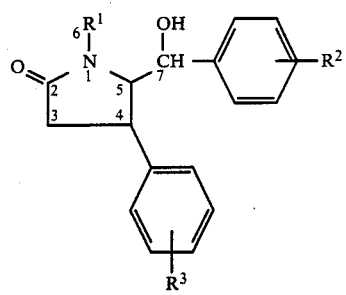

in which
R$^1$, R$^2$ and R$^3$ have the abovementioned meaning, are oxidized in inert organic solvents in the presence of a base, if appropriate in the presence of an auxiliary.

It is surprising that exclusively the C(3)–C(4)-trans-configurated hydroxylation product (I) is formed in a good yield with the aid of the process according to the invention. The process according to the invention has the advantage that relatively large amounts of substance can be made available in a short time and with little expenditure. In addition, it is possible to determine the stereochemistry of the end products by choosing the starting compound (II), that is to say to prepare individual stereoisomers in a controlled manner.

DETAILED DESCRIPTION OF THE INVENTION

In the present specification, the "alkyl" and "alkoxy" groups preferably contain up to 6 carbon atoms, "aryl", "aralkyl", "aryloxy" and "aralkoxy" preferably denote phenyl, benzyl, phenoxy and benzyloxy, respectively, and "acyl" groups preferably contain up to 7 carbon atoms.

Compounds of the formula (I) which are particularly preferably prepared by the process according to the invention are those in which
R$^1$ represents the alkyl with up to 4 carbon atoms and
R$^2$ and R$^3$ are identical or different and represent alkyl with up to 4 carbon atoms, alkoxy with up to 4 carbon atoms, phenyl, benzyl, phenoxy, benzyloxy, benzoyl, acetyl, trifluoromethyl, trifluoromethoxy, nitro, fluorine, chlorine, bromine, hydroxyl, amino, dimethylamino, diethylamino, acetylamino, carboxyl or sulpho,
in the form of their isomers, isomer mixtures, racemates or optical antipodes.

If, for example, (±) 4(S*), 5(R*), 7(S*)-5-α-hydroxybenzyl-1-methyl-4-phenylpyrrolidin-2-one is used as the starting substance, the course of the reaction can be illustrated by the following equation:

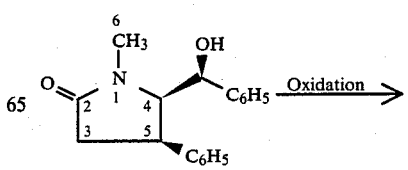

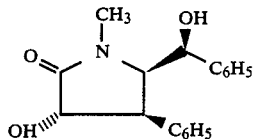

Oxidizing agents which can be employed are organic or inorganic peroxo compounds, such as, for example, peroxoacetic acid, chloroperbenzoic acid or a molybdenum peroxide/pyridine complex, and in addition oxygen, ozone or oxygen transfer agents, such as, for example, 2-sulphonyloxaziridine.

Possible solvents are the customary inert organic solvents which do not change under the reaction conditions. These include, preferably, hydrocarbons, such as, for example, benzene, toluene, xylene, hexane, cyclohexane or petroleum fractions, ethers, such as, for example, diethyl ether, tetrahydrofuran or dioxane, alcohols, such as, for example, methanol, ethanol or propanol, halogenohydrocarbons, such as, for example, methylene chloride, chloroform, carbon tetrachloride or 1,2-dichloroethane, glacial acetic acid or hexamethylphosphoric acid triamide. It is also possible to use mixtures of the solvents mentioned.

The bases customary for enolate formation can be used as the bases. These include, preferably, alkali metal alcoholates, alkali metal amides, alkali metal hydrides or organo-alkali metal compounds, such as, for example, sodium or potassium methanolate, sodium or potassium ethanolate, potassium tert.-butanolate, sodium hydride, sodium amide, lithium diisopropylamide, butyl-lithium or phenyl-lithium. It is likewise possible to employ tertiary amines, such as, for example, 1,5-diazabicyclo(4,3,0)non-5-ene or 1,8-diazabicyclo(5,4,0)undec-7-ene. Particularly preferred bases are lithium diisopropylamide, lithium hexamethylpiperidide and n-, sec.- or tert.-butyl-lithium and phenyl-lithium.

The choice of base, solvent and, if appropriate, auxiliary depends on the oxidation method selected.

Auxiliaries which are used are, if appropriate, substances which are capable of reducing hydroperoxide intermediates formed in situ, in particular if molybdenum peroxide/pyridine or oxygen is used as the oxidizing agent. Phosphites are preferably used for this, in particular trialkyl or triaryl phosphites, such as, for example, trimethyl phosphite, triethyl phosphite, tripropyl phosphite, triisopropyl phosphite, tributyl phosphite or triphenyl phosphite.

Oxidation with molybdenum peroxide/pyridine in hexamethylphosphoric acid triamide and with oxygen, in each case using phosphites as an auxiliary, is particularly suitable. Especially good yields are obtained in the oxidation with oxygen in a solvent, such as tetrahydrofuran or hexamethylphosphoric acid triamide, or if appropriate mixtures thereof, using triethyl phosphite as the auxiliary. It has proved advantageous here to use lithium diisopropylamide or butyl-lithium as the base.

The reaction temperatures can be varied between $-100°$ C. and $+20°$ C. The reaction is preferably carried out in a temperature range from $-78°$ C. to $0°$ C.

The hydroxylation by the process according to the invention can be carried out under normal pressure and also under increased or reduced pressure. In general, it is carried out under normal pressure.

In carrying out the process according to the invention, 1 to 5, preferably 1 to 2.5, moles of base and 0.5 to 5, preferably 0.5 to 2, moles of the auxiliary are employed per mole of the starting compound.

The enolate of (II) is usually first prepared in a suitable solvent with the aid of the base and absolute oxygen is passed through the solution, with the addition of phosphite, until no further change can be observed by thin layer chromatography. The reaction mixture is worked up in the customary manner familiar to the expert.

The starting compounds of the formula (II) are new. They can be prepared by a process in which aldehydes of the general formula (III)

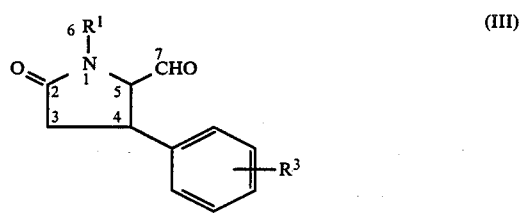

in which
R$^1$ and R$^3$ have the abovementioned meaning, are reacted with compounds of the general formula (IV)

in which
R$^2$ has the abovementioned meaning and
X represents MgBr, MgCl, Li or Ti[OCH(CH$_3$)$_2$]$_3$, in suitable inert organic solvents in a temperature range from $-20°$ C. to $+50°$ C., preferably from $-10°$ C. to $+30°$ C., and, if appropriate, the product is epimerised on carbon atom 7.

Compounds of the formula (IV) in which X represents MgCl, MgBr or Ti[OCH(CH$_3$)$_2$]$_3$ are particularly suitable.

Suitable solvents are all the inert organic solvents which are usually employed in reactions with organometallic reagents. These include, preferably, ethers, such as diethyl ether or tetrahydrofuran, if appropriate mixed with hexane.

The reaction can be carried out by a process analogous to those known from the literature, such as are described, for example, by D. Seebach, B. Weidmann and L. Widler in "Modern Synthetic Methods 1983", page 217 et seq. (Verlag Salle und Sauerländer) or in Houben Weyls "Methoden der organischen Chemie" ("Methods of Organic Chemistry") Volume XIII/2a, page 289 et seq., page 302 et seq., or by N. L. Drake and G. B. Woke in *Organic Synthesis, Coll. Vol. II*, 406 et seq. (1963).

The compounds of the formula (III) can be employed in the reaction in the form of their isomers, isomer mixtures, racemates or optical antipodes. The on C(4)-C(5)-cis-configurated compounds of the formula (III) are preferably employed.

Depending on the nature of the organometallic reagent used, the compounds which are R-configurated on carbon atom 7, of the general formula (IIa)

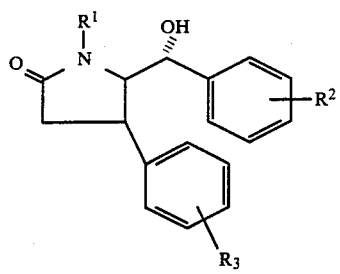

in which

R[1], R[2] and R[3] have the abovementioned meaning, can first be formed, and are epimerized by oxidation to compounds of the general formula (V)

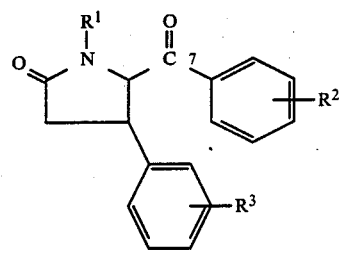

in which

R[1], R[2] and R[3] have the abovementioned meaning, and subsequent reduction of (V) to give 7-S-configurated compounds of the general formula (IIb)

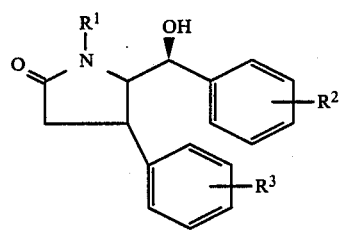

in which

R[1], R[2] and R[3] have the abovementioned meaning.

The oxidation of (IIa) to (V) is carried out by a process analogous to known processes with dimethylsulphoxide as the oxidizing agent, with the addition of anhydrides, in particular trifluoroacetic anhydride, in suitable organic solvents, in particular in halogenohydrocarbons, such as, for example, methylene chloride or chloroform, or hydrocarbons, such as benzene, toluene, xylene or hexane, or in ethers, such as diethyl ether, dioxane or tetrahydrofuran, or in mixtures of the solvents mentioned, such as is described, for example, by S. L. Huang, K. Omura and D. Swern in *Synthesis*, 1980, 297.

The reduction of (V) to (IIb) can be carried out with the customary reducing agents. Metal hydrides and complex metal hydrides, such as, for example, lithium boranate, lithium hydridoborates, sodium hydridoborates, boranes, sodium hydridoaluminates, lithium hydridoaluminates or tin hydrides, are particularly suitable for this. Lithium hydridoborates, such as, for example, lithium hydrido-triethyl-borate or lithium-hydridotris(1-methylpropyl)borate, or sodium borohydride are particularly preferably employed.

Suitable solvents are the customary inert organic solvents used in reductions with hydrides. These are preferably ethers, such as diethyl ether and tetrahydrofuran. The reduction is carried out by a method analogous to known methods (W. Friedrichsen in Houben-Weyl's "Methoden der organischen Chemie ("Methods of Organic Chemistry) VIII/1b, 145 et seq.; H. C. Brown, S. Krishnamurthy, *Chem. Commun.*, 1972, 868; and A. Hajos in Houben-Weyl's "Methoden der organischen Chemie ("Methods of Organic Chemistry) IV/1d, 267 et seq.).

The compounds (IIa) can also be epimerized by a process analogous to other known processes, such as are described, for example, by O. Mitsunobu in *Synthesis*, 1981, 1 et seq.

If, for example, (±)-(4R*), (5R*)-5-formyl-1-methyl-4-phenylpyrrolidin-2-one is used as the starting substance, the reaction can be represented by the following equation:

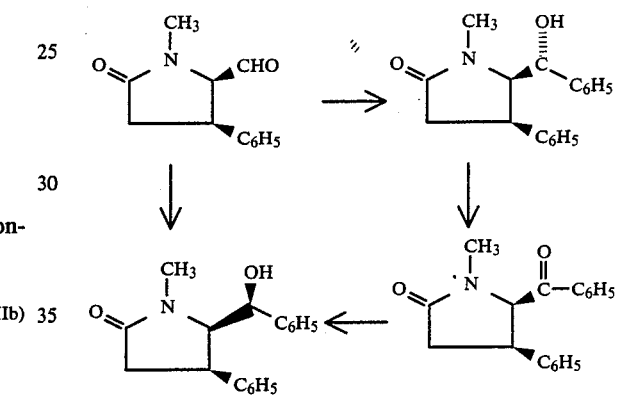

If the readily accessible Grignard compounds (X in IV represents MgCl or MgBr) are used as the organometallic reagents, exclusively the compounds IIa having the 7-R-configuration are formed, and these can be epimerised in the manner described. Both the 7-R- and the 7-S-configurated compounds and the isomers, isomer mixtures, racemates and optical antipodes thereof can be hydroxylated according to the invention to give compounds I.

The organometallic compounds of the formula IV are known or can be prepared by known mthods (K. Nützel in Houben-Weyl's "Methoden der organischen Chemie" ("Methods of Organic Chemistry") XIII/2a 47 et seq.).

The aldehydes of the general formula (III) are new and can be prepared in accordance with the following equation:

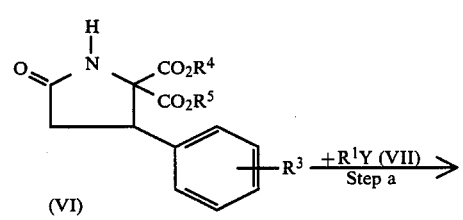

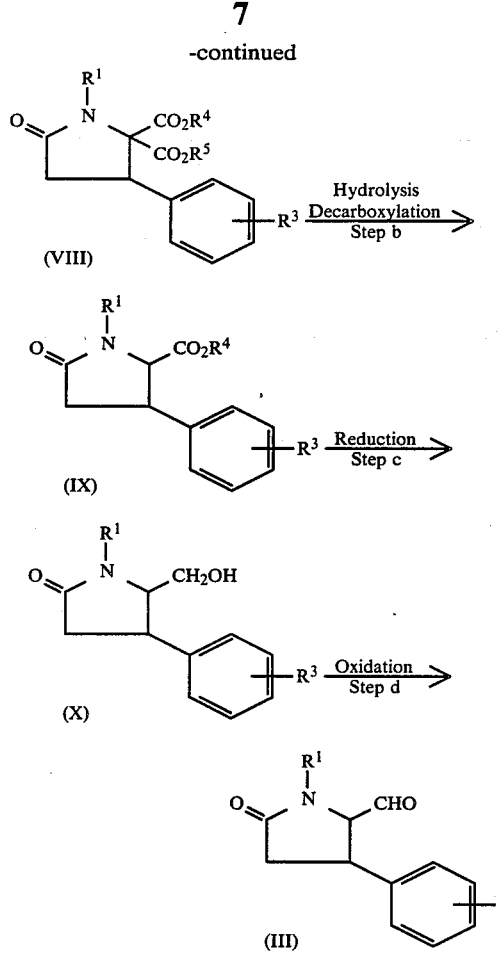

(VIII)

(IX)

(X)

(III)

($R^1$ and $R^3$ have the abovementioned meaning and $R^4$ and $R^5$ are identical or different and represent $C_1$–$C_4$-alkyl).

According to this equation, compounds of the general formula (VI) are reacted in step a with compounds of the general formula (VII)

$R^1$—Y  (VII)

in which $R^1$ has the abovementioned meaning and

Y represents halogen, preferably bromine or iodine, a diazo group or a group of the formula

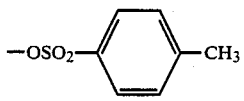

or —$OSO_2OCH_3$, preferably iodine, if appropriate in the presence of a base, such as sodium, sodium hydride, sodium amide, butyl-lithium or lithium diisopropylamide, in suitable solvents, such as diethyl ether, tetrahydrofuran, dimethylformamide or hexamethylphosphoric acid triamide, at temperatures from −20° C. to +80° C., preferably from 0° C,. to +40° C. Dimethylformamide is especially suitable as the solvent. It has proved advantageous here to use sodium hydride as the base. The reaction is carried out and the product is worked up by customary methods familiar to the expert.

In step b, the compounds of the general formula VIII (obtained from VI) are hydrolyzed and decarboxylated by a process analogous to that described by P. Pachaly in *Chem. Ber.*, 104 (2), 412–39 (1971), and the isomer mixture of (IX) thereby formed ($C_{(4)}$–$C_{(5)}$-cis or -trans) is separated, if appropriate, by generally known methods of chromatography or by recrystallization. The subsequent reactions can be carried out either with the isomer mixture or with the individual cis- or trans-isomers. Preferably, the mixture IX is separated and the subsequent reactions are carried out with the individual isomers, preferably with the C(4)–(5)-cis-configurated isomers.

The reduction of the compounds of the formula IX to compounds of the formula X (step c) is carried out by the same method and under the same condition as has already been described for the reduction of the compounds (V) to the compounds (IIb).

The oxidation of compounds of the formula X to compounds of the formula III (step d) is carried out by the same methods and under the same conditions as have already been described for the oxidation of compounds of the formula (IIa) to compounds of the formula (V).

The starting compounds of the formula VI are known from the literature or can be prepared by methods which are known from the literature [G. H. Cocolas, W. H. Hartung, *J. Am. Chem. Soc.*, 79, 5203 (1957); and F. Zymalkowski, P. Pachaly, *Chem. Ber.*, 100, 1137 (1967)].

The following equation is intended to illustrate the overall synthesis of the end products of the formula (I) with all possible intermediate compounds (II)–(X):

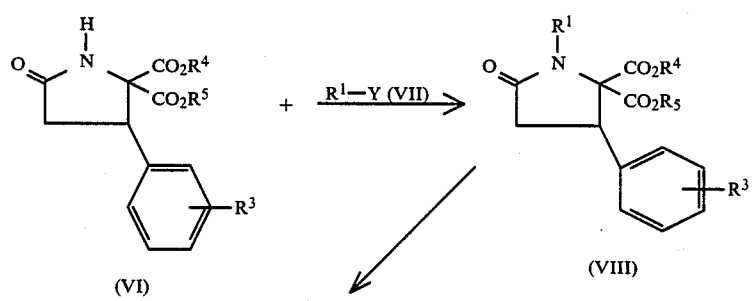

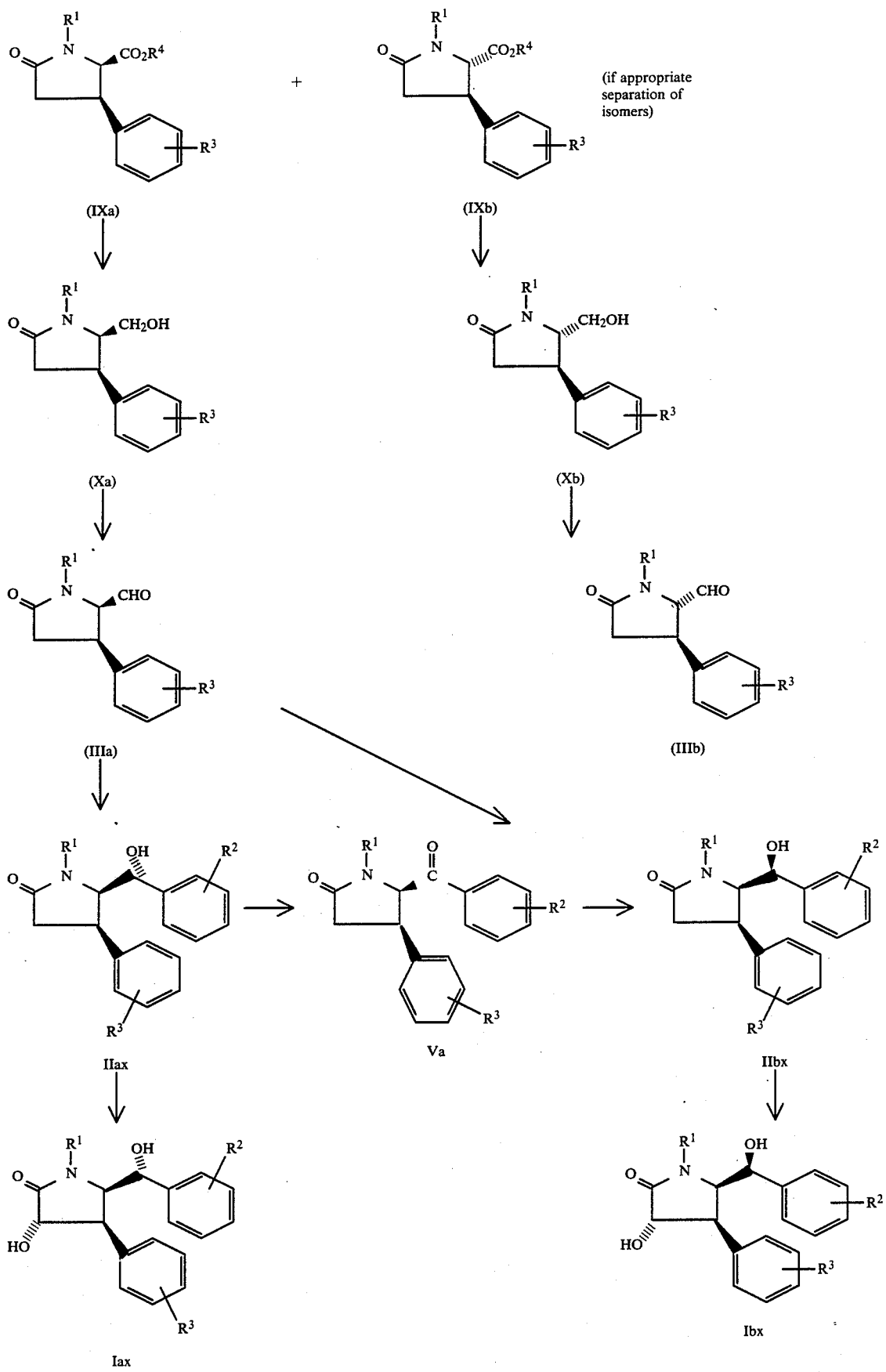

-continued
(IIIb)

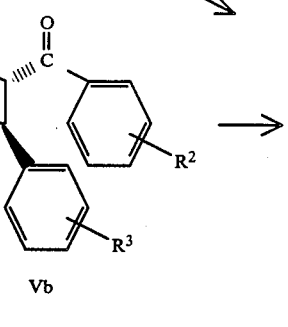

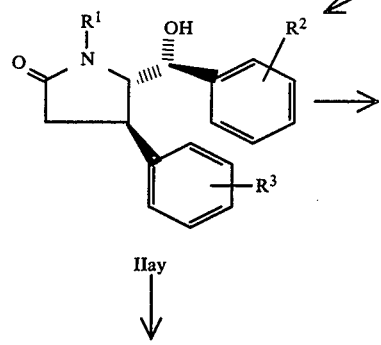

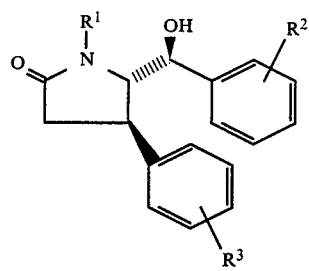

Iay

Iby

The invention will now be described with reference to the following non-limiting examples.

PREPARATION EXAMPLES

EXAMPLE 1

(±)5,5-Diethoxycarbonyl-4-phenylpyrrolidin-2-one

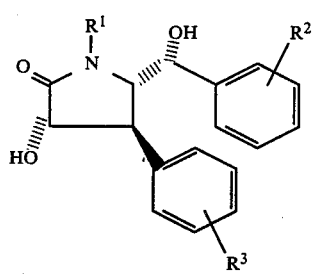

A solution of 18 g (0.8 gram atoms) of sodium in 400 ml of absolute ethanol was added dropwise to a suspension of 432 g (2 moles) of diethyl acetamidomalonate in 1.6 l of absolute ethanol at room temperature under an $N_2$ atmosphere. 564 g (3.2 moles) of ethyl cinnamate were slowly added and the mixture was then heated at the boiling point for 24 hours.

For working up, the mixture was allowed to come to room temperature, 2.5 l of chloroform were added and the mixture was neutralized with acetic acid. It was washed thoroughly with water (5× in each case 500 ml), dried over $MgSO_4$ and concentrated on a rotary evaporator. The oily residue was dissolved in a little acetone, hexane was added until crystallization occurred, and further hexane was then added until no further cloudiness was to be observed at the dropwise addition point. Filtration with suction gave 398 g (54%) of the title compound of melting point 97°–99° C. Chromatography of the mother liquor (toluene/ethyl acetate) gave a further 85 g (14%) of the title compound, total yield 413 g (68%).

IR(KBr): $\nu=1770$ (ester), 1700 (amide).

$^1$H-NMR (300 MHz, CDCl$_3$): $\delta=0.84$ and 1.28 (in each case t, J=7.5 Hz; 6H, CH$_2$CH$_3$); ABX signal: $\delta_A=2.63$, $\delta_B=2.96$ ($J_{AB}=17.3$ Hz, $J_{AX}=6$ Hz, $J_{BX}=9$ Hz; 2H, C(3)-H); 3.66 and 3.71 (in each case m, 2H, cis-CH$_2$CH$_3$); 4.28 (m, 2H, trans-CH$_2$CH$_3$); 4.39 (dd, $J_{AX}=6$ Hz, $J_{BX}=9$ Hz, 1H, C(4)-H); 6.95 (br, 1H, NH); and 7.39 (br, 5H, C$_6$H$_5$).

EXAMPLE 2

(±) 5,5-Diethoxycarbonyl-1-methyl-4-phenyl-pyrrolidin-2-one

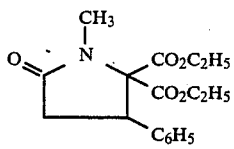

A solution of 100 g (0.33 mole) of (±) 5,5-diethoxycarbonyl-4-phenylpyrrolidin-2-one in 500 ml of absolute dimethylformamide was added dropwise to a suspension of 9.64 g (0.36 mole) of sodium hydride in 200 ml of absolute dimethylformamide at room temperature under an N$_2$ atmosphere. The mixture was subsequently stirred at room temperature until the evolution of gas had ended, a solution of 93.7 g (0.66 mole) of methyl iodide in 50 ml of absolute dimethylformamide was then added and the mixture was stirred at room temperature until all the starting material had reacted (about 1 hour, thin layer chromatography check). The reaction mixture was poured into 2 l of buffer solution, pH=7, and extracted five times with 600 ml of diethyl ether each time.

Drying of the organic extracts (MgSO4) and stripping off of the solvent in vacuo gave 105 g (99.6%) of the title compound (95% pure according to the $^H$-NMR spectrum), which was further reacted directly. A sample was distilled in a bulb tube (boiling point$_{0.5}$: 240° C.) for analysis, R$_f$: 0.36 (toluene/ethyl acetate: 2/1).

IR (film): $\nu=1735$ (ester), 1700 (amide).

$^1$H-NMR (500 MHz, CDCl$_3$): $\delta=0.9$ and 1.33 (in each case t, J=7.5 Hz; 6H, CH$_2$CH$_3$); ABX signal; $\delta_A=2.66$, $\delta_B=3.0$ (J$_{AB}$=18 Hz, J$_{AX}$=6 Hz, J$_{BX}$=8.3 Hz; 2H, C(3)-H); 3.06 (s; 3H, N-CH); 3.62 and 3.79 (in each case m, 2H, cis-CH$_2$CH$_3$); 4.31 (m, 3H, trans-CH$_2$CH$_3$) and C(4)-H); and 7.26 (m, 5H, C$_6$H$_5$).

EXAMPLE 3

($\pm$)-4-(R*),5(R*) [I] and ($\pm$)-4(R*),5(S*)-5-ethoxycarbonyl-1-methyl-4-phenylpyrrolidin-2-one [II]

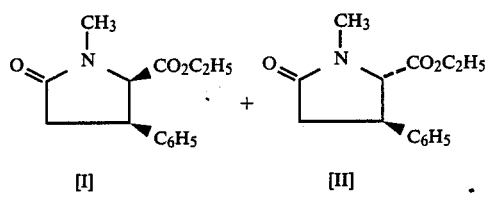

[I]   [II]

49.5 g (0.156 mole) of barium hydroxide octahydrate were heated in 483 ml of distilled water at 70° C. until an almost clear solution is formed. A solution of 100 g (0.313 mole) of ($\pm$)5,5-diethoxycarbonyl-1-methyl-4-phenyl-pyrrolidin-2-one in 724 ml of ethanol was added (clear solution) and the mixture was subsequently stirred at 70° C. for 20 minutes until the starting material had reacted completely (about 20 minutes, thin layer chromatography check). The mixture was cooled and acidified to pH=1-2, while cooling with ice, and the ethanol was stripped off in vacuo (bath temperature 30°-40° C.). The solid was filtered off with suction and the aqueous phase was extracted, with addition of sodium chloride, 3 times with 200 ml of ethyl acetate each time. Drying and stripping off of the solvent gave a residue which was combined with the solid obtained above, and the mixture was dried in a desiccator over P$_4$O$_{10}$ under a high vacuum for 24 hours. The solid was then heated to 170° C. in an oil bath, while stirring thoroughly, until the evolution of gas had ended (5-10 minutes). Cooling and flash chromatography (cyclohexane/ethyl acetate=1/1, finally with ethyl acetate) gave 39.3 g (50.7%) of the cis-product I with R$_f$=0.10 and 19.6 g (25.3%) of the trans-product II with R$_f$=0.20 (in each case in cyclohexane/ethyl acetate 1/1).

IR(KBr): $\nu=1736$, 1690 cm$^{-1}$.

$^1$H-NMR (200 MHz, CDCl$_3$) [I]: $\delta=0.83$ (t, J=7.5 Hz, 3H, CH$_2$CH$_3$) ABX signal: $\delta_A=2.67$, $\delta_B=2.95$ (J$_{AB}$=17.5 Hz, J$_{AX}$=9 Hz, J$_{BX}$=10 Hz, 2H, C(3)-H), 2.87 (s, 3H, N-CH$_3$), 3.75 (m, 2H, CH$_2$CH3); 3.91 (q, J=9-10 Hz, 1H, C(4)-H), 4.36 (d, J=9 Hz, 1H, C(5)-H), 7.28 (m, 5H, C$_6$H$_5$).

[II]: $\delta=1.30$ (t, J=7.5 Hz, 3H, CH$_2$CH$_3$); ABX signal: $\delta$A=2.54, $\delta$B=2.82 (J$_{AB}$=18.5 Hz, J$_{AX}$=5 Hz, J$_{BX}$=9 Hz, 2H, C(3)-H), 3.80 (s, 3H, N-CH$_3$), 3.53 (ddd, J=9 Hz, J=5 Hz, J=4 Hz, 1H, C(4)-H), 4.07 (d, J=4 Hz, 1H, C(5)-H), 4.27 (m, 2H, CH$_2$—CH$_3$) 7.3 (m, 5H, C$_6$H$_5$).

EXAMPLE 4

($\pm$) 4(R*),5(R*)-5-Hydroxymethyl-1-methyl-4-phenylpyrrolidin-2-one

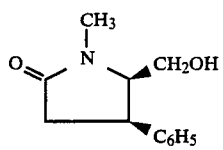

0.317 mole of LiB(Et)$_3$H (as a 1M solution in tetrahydrofuran, 316.9 ml) was added dropwise to a solution of 39.2 g (0.159 mole) of ($\pm$) 4(R*),5(R*)-5-ethoxycarbonyl-1-methyl-4-phenylpyrrolidin-2-one in 390 ml of absolute tetrahydrofuran at $-15°$ to $-20°$ C. under an N$_2$ atmosphere.

The reaction mixture was subsequently stirred at 0° C. for 1 hour, poured into about 200 ml of ice-cold 2N hydrochloric acid and extracted twice with 200 ml of ethyl acetate each time. The aqueous phase was saturated with sodium chloride and extracted twice more with 200 ml of ethyl acetate each time. The collected organic extracts were washed with a little water, dried over MgSO$_4$ and concentrated on a rotary evaporator. The residue was made to crystallise with a little ether and the product was then precipitated with pentane until no further cloudiness was to be observed at the dropwise addition point. After filtration with suction and drying, 29.1 g (89.2%) of the title compound of melting point 93°-95° C. were obtained.

IR(KBr): $\nu=3324$, 1687 cm$^{-1}$.

$^1$H-NMR (300 MHz, CDCl$_3$): $\delta=$AB-part of ABM system, $\delta_A=2.59$, $\delta_B=2.97$ (in each case dd, J$_{AB}$=15 Hz, J$_{AM}$=7.5 Hz, J$_{BM}$=9 Hz, 2H, C(3)-H; 2.97 (s, 3H, N-CH$_3$) AB-part of ABM system, $\delta_A=3.36$, $\delta_B=3.62$ (in each case dd, J$_{AB}$=11.2 Hz, J$_{AM}$=J$_{BM}$=3 Hz, 2H, C(7)-H); 3.72-3.85 (m, 2H, C(4)-H, C(5)-H); 7.32 (m, 5H, C$_6$H$_5$).

EXAMPLE 5

($\pm$)4(R*),5(R*)-5-Formyl-1-methyl-4-phenylpyrrolidin-2-one

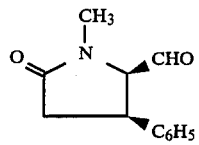

A solution of 29.7 ml of trifluoroacetic anhydride in 56 ml of absolute methylene chloride was added dropwise at $-60°$ C. to a solution of 19.9 ml (0.28 mole) of absolute dimethylsulphoxide in 140 ml of absolute methylene chloride under an N$_2$ atmosphere in the course of 10 minutes. The mixture was stirred at this temperature for 15 minutes and a solution of 28.8 g (0.140 mole) of ($\pm$)4(R*),5(R*)-5-hydroxy-methyl-1-methyl-4-phenyl-pyrrolidin-2-one in 250 ml of methylene chloride was added dropwise such that the temperature did not exceed $-60°$ C. The mixture was subsequently stirred at $-60°$ C. for 90 minutes, warmed briefly to $-30°$ C. (5-10 minutes) and cooled again to $-60°$ C. 56 ml of absolute triethylamine were slowly added at this temperature and the mixture was stirred at $-60°$ C. for 30 minutes and warmed to room temperature. 600 ml of water were added, the phases were separated and the aqueous phase was extracted three times with 250 ml of methylene chloride each time. The collected organic extracts were washed twice with 300 ml of water each time, dried over magnesium sulphate and the solvent was stripped off (in vacuo). 28.3 g (100%) of the title compound with $R_f$=0.25 (ethyl acetate) (91% pure according to the $^1$H-NMR spectrum) were obtained. The crude product thus obtained was further reacted directly, after drying (24 hours, high vacuum).

IR (CHCl$_3$): $\nu$=1734, 1689 cm$^{-1}$.

$^1$H-NMR (300 MHz, CDCl$_3$): $\delta$2.79 (dd, J=5.3 Hz, J=9.7 Hz, 2H, C(3)-H); 2.91 (s, 3H, N-CH$_3$); 4.02 (q, J=9.7 Hz, 1H, C(4)-H); 4.30 (dd, J=1 Hz, J=9.7 Hz, 1H, C(5)-H); 7.3 (m, 5H, C$_6$H$_5$), 9.17 (d, J=1 Hz, 1H, CHO).

EXAMPLE 6

(±)4(R*),5(R*),7(R*)-5-α-Hydroxybenzyl-1-methyl-4-phenylpyrrolidin-2-one

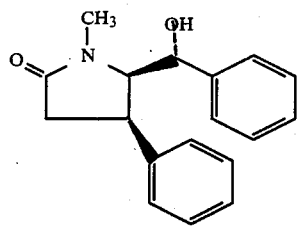

A solution of 24.8 g (16.7 ml, 0.156 mole) of bromobenzene in 44 ml of absolute tetrahydrofuran was added dropwise to 3.84 g of Mg filings under N$_2$ such that the tetrahydrofuran simmered. 100 ml of absolute tetrahydrofuran were then added and the mixture was heated at the boiling point under reflux until all the magnesium had dissolved (1-2 hours).

The mixture was cooled to 0° C. and a solution of 24.7 g (0.12 mole) of (±) 4(R*),5(R*)-5-formyl-1-methyl-4-phenylpyrrolidin-2-one in 250 ml of absolute tetrahydrofuran was added dropwise, with vigorous stirring, such that the temperature did not exceed 5° C. If necessary, absolute tetrahydrofuran had to be added for better stirrability. The reaction mixture was then stirred at 0°-5° C. for 1 hour, poured onto 350 ml of 0.5N HCl-ice and extracted four times with 300 ml of ethyl acetate each time and twice with 300 ml of methylene chloride each time. The collected ethyl acetate and methylene chloride extracts were washed (separately!) twice with 200 ml of water each time, combined and dried over magnesium sulphate. The residue which remained after stripping off of the solvent (in vacuo) was triturated with 100 ml of ether until crystallization occurred. 500 ml of pentane were then slowly added and the mixture was left to stand overnight in a refrigerator. Filtering off of the solid with suction gave 25 g (74.3%) of the title compound of melting point: 210°-212° C.

For analysis, the product was recrystallized from acetone (melting point: 214°-5° C.).

IR(KBr) $\nu$=3362 (br), 1654 cm$^{-1}$.

$^1$H-NMR (300 MHz, d$_6$-DMSO): $\delta$=2.21 (s, 3H, NCH$_3$); 2.24 (dd, A-part of ABM system, $J_{AB}$=15.7 Hz, $J_{AM}$=9.4 Hz, 1H, cis-C(3)-H); 3.05 (dd, B-part of ABM system, $J_{BM}$=12.7 Hz, 1H, trans-C(3)-H); 3.80 (dt, M-part of ABM system, $J_{AM}$=8.5 Hz, $J_{AB}$=12.7 Hz, $J_{4,5}$=8.5 Hz, 1H, C(4)-H); 4.15 (dd, J=8.5 Hz, J=1 Hz, 1H, C(5)-H); 4.26 (dd, J=6 Hz, J=1 Hz, 1H, C(7)-H); 5.35 (d, J=6 Hz, 1H, OH); 7.15-7.5 (m, 10H, C$_6$H$_5$).

EXAMPLE 7

(±)4(R*),5(R*)-5-Benzoyl-1-methyl-4-phenylpyrrolidin-2-one

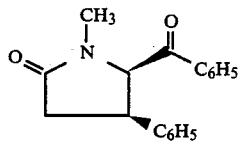

A solution of 18 ml of trifluoroacetic anhydride in 34 ml of absolute methylene chloride was added dropwise to a solution of 12.24 ml (0.171 mole) of absolute dimethylsulphoxide in 87 ml of absolute methylene chloride at −60° C. under an N$_2$ atmosphere in the course of 10 minutes. The mixture was subsequently stirred at this temperature for 15 minutes and a solution of 24 g (0.085 mole) of (±)4(R*),5(R*),7(R*)-5-α-hydroxybenzyl-1-methyl-4-phenylpyrrolidin-2-one in about 700 ml of absolute methylene chloride was added dropwise such that the temperature did not exceed −60° C. The mixture was subsequently stirred at −60° C. for 90 minutes, warmed briefly to −30° C. (9–10 minutes) and cooled again to −60° C. 34.2 ml of triethylamine were slowly added at this temperature and the mixture was stirred at −60° C. for 20 minutes and warmed to room temperature. 370 ml of water were added, the phases were separated and the aqueous phase was extracted three times with 250 ml of methylene chloride each time. The combined organic extracts were washed twice with 300 ml of water each time, dried over magnesium sulphate and concentrated on a rotary evaporator. The residue was evaporated in a rotary evaporator twice with 200 ml of ether each time. 23.5 g (100%) of the title compound were obtained as a solid of melting point: 115°-116° C. The crude product, which was pure according to the $^1$H-NMR spectrum, was further reacted directly.

For analysis, a sample was chromatographed over silica gel with ethyl acetate ($R_f$=0.25 ), melting point: 121°-2° C.

IR(KBr): $\nu$=1695, 1682 cm$^{-1}$.

$^1$H-NMR (300 MHz, CDCl$_3$) $\delta$=2.78 and 2.91 (AB-part of ABM spectrum, $J_{AB}$=16.5 Hz, $J_{AM}$=$J_{BM}$ 8.3 Hz, 2H, C(3)-H; 2.88 (s, 3H, N-CH$_3$); 4.02 (q, J=8.3 Hz, 1H, C(4)-H); 5.42 (d, J=8.3 Hz, 1H, C(5)-H); 7.0, 7.21, 7.59 and 7.50 (in each case m, 10H, C$_6$H$_5$).

EXAMPLE 8

(±)4(R*),5(R*),7(S*)-5-α-Hydroxybenzyl-1-methyl-4-phenylpyrrolidin-2-one

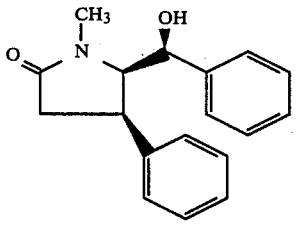

83 mmol of LiB(Et)$_3$H (83 ml of a 1M solution in tetrahydrofuran) were added dropwise to a solution of 23 g (82.3 mmol) of (±) 4(R*),5(R*)-5-benzoyl-1-methyl-4-phenylpyrrolidin-2-one in 200 to 270 ml of absolute tetrahydrofuran at −15° to −20° C. under an N₂ atmosphere. The reaction mixture was subsequently stirred at 0° C. for 1 hour, poured into 100 ml of ice-cold 1N HCl and extracted twice with 200 ml of ethyl acetate each time. The aqueous phase was saturated with sodium chloride and extracted twice more with 200 ml of ethyl acetate each time. The combined organic extracts were dried over MgSO₄ and concentrated on a rotary evaporator. The residue was dissolved in methylene chloride and washed twice with 100 ml of water each time. The organic phase was dried (MgSO₄) and concentrated on a rotary evaporator. The residue was made to crystallize with 100 ml of ether, and pentane was then slowly added, with stirring, until no further cloudiness was to be observed at the dropwise addition point. The precipitate was filtered off with suction and dried. 16.6 g (72%) of the title compound of melting point: 189°–195° C. were obtained.

The product is 95% pure according to ¹H-NMR and was further reacted directly.

For analysis, the product was recrystallized from acetone (melting point: 197°-8° C.)

IR(KBr): ν=3251, 1692 cm⁻¹.

¹H-NMR (300 MHz, DMSO): δ=1.97 and 2.05 (ABM signal, $J_{AB}$=13.5 Hz, $J_{AM}$=8.2 Hz, $J_{BM}$=13 Hz, 2H, C(3)-H); 2.91 (s, 3H, N-CH₃); 3.82 (dt, $J_{AM}$=$J_{4.5}$=8.2 Hz, $J_{BM}$=13 Hz, 1H, C(4)-H); 4.27 (dd, J=8.2 Hz, J=1.5 Hz, 1H, C(5)-H); 4.65 (dd, J=1.5 Hz, J=3.5 Hz, 1H, C(7)-H); 5.34 (d, J=3.5 Hz, 1H, OH); 6.70, 7.11 and 7.25 (in each case m, 10H, C₆H₅).

EXAMPLE 9

(±)3(S*),4(R*),5(R*),7(S*)-3-Hydroxy-5-α-hydroxybenzyl-1-methyl-4-phenylpyrrolidin-2-one (clausenamide)

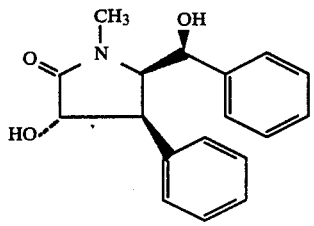

A solution of 17.7 g (62.8 mmol) of (±)4(R*),5(R*),7(*)-5-α-hydroxybenzyl-1-methyl-4-phenylpyrrolidin-2-one in 490 ml of absolute tetrahydrofuran and 130 ml of absolute hexamethylphosphoric acid triamide was introduced into a flask which had been heated thoroughly in vacuo and flushed with pure nitrogen, and the solution was cooled to −70° C. A solution of 0.152 mole of lithium diisopropylamide in 180 ml of absolute tetrahydrofuran/hexane (prepared from 22.1 ml of diisopropylamine in 80 ml of tetrahydrofuran by addition of 103 ml of a 1.5N solution of n-butyl-lithium in hexane at −20° C. to 0° C.) was added dropwise at this temperature. The mixture was subsequently stirred at −70° C. to −60° C. for 1 hour, 5.3 ml of freshly distilled trimethyl phosphite (dissolved in a little absolute tetrahydrofuran) were added and absolute oxygen (dried over H₂SO₄ and P₄O₁₀) was passed in (50-100 ml/minute). As soon as the product/starting material ratio no longer changed (2–3 hours) according to thin layer chromatography check (SiO₂; ethyl acetate/MeOH: 2/1; $R_f$=0.3 for the title compound, $R_f$=0.37 for the starting compound, staining with molybdatophosphoric acid spray reagent, the mixture was poured onto 600 ml of 0.5N HCl, while cooling with ice, and if appropriate acidified to pH 3 to 4.

The phases were separated and the aqueous phase was extracted four times with 300 ml of ethyl acetate each time. The combined organic extracts were washed three times with 300 ml of water each time, dried over MgSO₄ and concentrated on a rotary evaporator. The residue was taken up in 50–100 ml of ether, the mixture was stirred until crystallization started and pentane was slowly added, with stirring, until no further cloudiness was to be observed at the dropwise addition point. The mixture was left to stand overnight in a refrigerator and filtered with suction. about 17 g of a crude solid which, in addition to the title compound, contained about 35–40% of starting material were obtained. For purification, the product is recrystallized twice from methanol. The title compound is then obtained in a purity of about 95%. Chromatography over aluminium oxide (neutral) proceeds without losses and with recovery of the pure starting material. For this, the crude product is absorbed onto silica gel (dissolving in MeOH under the influence of heat, addition of 5 parts by weight of silica gel, concentration on a rotary evaporator and evaporation on a rotary evaporator several times with ethyl acetate until an MeOH-free product as dry as dust results). The adsorbate is introduced onto a column containing Al₂O₃ (neutral, 50 parts by weight) and the starting material is eluted first with ethyl acetate (flash chromatography, check by thin layer chromatography and analytical high performance liquid chromatography). The title compound is then eluted with ethyl acetate/methanol mixtures (40/1, 20/1 and then 10/1). 8.6 g (46.1%) of the title compound of melting point: 236°–7.5° C. (authentic clausenamide: 236°–7° C.) and a purity of about 98% (according to ¹H-NMR, contains about 2% of starting material) were obtained. It was possible to recover 5 g of the pure starting material.

IR(KBr): ν=3402, 3321, 1689 cm⁻¹.

¹H-NMR (300 MHz, DMSO): δ=3.01 (s, 3H, N-CH₃); 3.50 (dd, J=8 Hz, J=10.5 Hz, 1H, C(4)-H); 3.82 (dd, J=10 Hz, J=7 Hz, 1H, C(3)-H); 4.30 (dd, J=8 Hz, J=2 Hz, 1H, C(5)-H); 4.65 (dd, J=2 Hz, J=3 Hz, 1H, C(7)-H); 5.39 (d, J=7 Hz, 1H, C(3)-OH); 5.45 (d, J=3 Hz, 1H, C(7)-OH); 6.61–6.64 (m, 2H, aromatic H) and 7.03–7.28 (m, 8H, aromatic H).

EXAMPLE 10

(±)3(S*),4(R*),5(R*),7(R*)-3-Hydroxy-5-α-hydroxybenzyl-1-methyl-4-phenylpyrrolidin-2-one (7-epi-clausenamide)

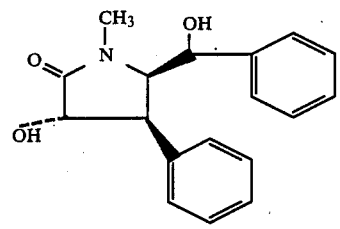

2 g (0.71 mole) of 4(R*),5(R*),7(R*)-5-α-hydroxybenzyl-1-methyl-4-phenylpyrrolidin-2-one gave, after precipitation with ether/pentane, 1.8 g of a solid which was chromatographed on silica gel with cyclohexane/ethyl acetate−½ ("flash" chromatography). 0.94 g (45%) of the pure title compound of melting point 200°–1° C. was obtained. It was possible to recover 0.7 g of the starting material.

IR(KBr): $\nu = 3435, 3363, 1660$ cm$^{-1}$.

$^1$H-NMR (300 MHz, DMSO) $\delta = 2.18$ (s, 3H, N-CH$_3$), 3.54 (dd, J=8 Hz, J=10 Hz, 1H, C(4)-H) 4.12 (d, J=8 Hz, 1H, 1H C(5)-H), 4.25 (d, J=6 Hz, 1H, C(7)-H), 4.93 (dd, J=10 Hz, J=7.5 Hz, 1H, C(3)-H), 5.43 (d, J=6 Hz, 1H, C(3)-OH), 5.47 (d, J=7.5 Hz, 1H, C(7)-OH) and 7.18–7.55 (m, 10H, aromatic H).

EXAMPLE 11

(±)4(R*),5(R*),7(R*)-5-(1-hydroxy-1-p-chlorophenyl)-methyl-1-methyl-4-phenylpyrrolidin-2-one

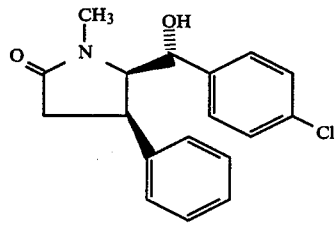

The procedure was analogous to Example 6, with the difference that the Grignard reagent was prepared in the ultrasonic bath. 15.12 g (0.079 mmol) of 4-chlorobromobenzene and 12.19 g (0.06 mol) of the title compound from Example 5 were used. After working up analogously to Example 6, the residue was taken up in a small amount of hot ethyl acetate and slowly cooled while grinding with a glass rod (concluding with ice bath). The reaction product was allowed to stand for 12 h and then filtered off with suction. 11.53 g (60.9% of theory) of the title compound were obtained of melting point: 201° C. (ether/pentane).

$^1$H-NMR (200 MHz, CDCl$_3$): $\delta = 2.44$ (s, 3H, NCH$_3$); 2.40 (dd, A-part of ABM system, $J_{AB}=15$ Hz, $J_{AM}=9.5$ Hz, 1H, cis-C(3)-H; 3.15 (dd, B-part of ABM system, $J_{BM}=12.5$ Hz, 1H, trans-C(3)-H); 3.78 (dt, M-part of ABM system, $J_{AM}=9.5$ Hz, $J_{BM}=12.5$ Hz, $J_{4.5}=7.5$ Hz, 1H, C(4)-H); 3.83 (d, J=6 Hz, 1H, OH); 3.97 (dd, J=7.5 Hz, J=1 Hz, 1H, C(5)-H); 4.39 (dd, J=6 Hz, J=1 Hz, 1H, C(7)-H); 7.12–7.38 (m, 9H, aromatic H).

EXAMPLE 12

(±)
4(R*),5(R*),7(R*)-5-(1-hydroxy-1-m-fluorophenyl)-methyl-1-methyl-4-phenylpyrrolidin-2-one

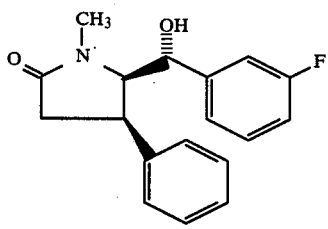

The procedure was analogous to Example 11. 13.83 g (0.079 mol) of 3-fluorobromobenzene and 12.19 g (0.06 mol) of the title compound from Example 5 were used. 11.73 g (70.9% of theory) of the title compound were obtained of melting point: 213° C. (ether/pentane).

$^1$H-NMR (200 MHz, CDCl$_3$/DMSO): $\delta = 2.45$ (s, 1H, N-CH$_3$); 2.40 (dd, A-part of ABM system, $J_{AB}=15$ Hz, $J_{AM}=9.5$ Hz, 1H, cis-C(3)-H); 3.20 (dd, B-part of ABM system, $J_{BM}=12.5$ Hz, 1H, trans-C(3)-H); 3.8 (dt, M-part of ABM system, $J_{AM}=9.5$ Hz, $J_{BM}=12.5$ Hz, $J_{4.5}=7.5$ Hz, 1H, C(4)-H); 4.03 (dd, J=7.5 Hz, J=1 Hz, 1H, C(5)-H); 4.36 (dd, J=6 Hz, J=1 Hz, 1H, C(7)-H); 5.03 (d, J=6 Hz, 1H, OH); 6.8–7.1 and 7.17–7.4 (in each case m, 9H aromatic H).

EXAMPLE 13

(±)
4(R*),5(R*),7(R*)-5-(1-hydroxy-1-m-chlorophenyl)-methyl-1-methyl-4-phenylpyrrolidin-2-one

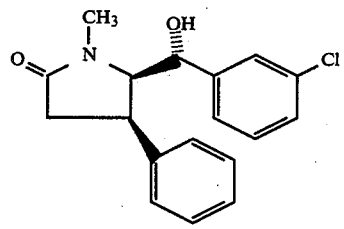

The procedure was analogous to Example 11. 15.12 g (0.079 mol) of 3-bromochlorobenzene and 12.19 g (0.06 mol) of the title compound from Example 5 were used. 12.2 g (64.4% of theory) of the title compound were obtained of melting point: 220° C.

$^1$H-NMR (200 MHz, CDCl$_3$/DMSO): $\delta = 2.43$ (s, 3H, NCH$_3$); 2.38 (dd, A-part of ABM system, $J_{AB}=15$ Hz, $J_{AM}=9.5$ Hz, 1H, cis-C(3)-H); 3.18 (dd, B-part of ABM system, $J_{BM}=12.5$ Hz, 1H, trans-C(3)-H); 3.81 (dt, M-part of ABM system, $J_{AM}=9.5$ Hz, $J_{BM}=12.5$ Hz, $J_{4.5}=7.5$ Hz, 1H, C(4)-H); 4.05 (dd, J=7.5 Hz, J=1 Hz, 1H, C(5)-H); 4.32 (dd, J=6 Hz, J=1 Hz, 1H, C(7)-H); 5.32 (d, J=6 Hz, 1H, OH); 7.12–7.45 (m, 9H, aromatic H).

EXAMPLE 14

(±)
4(R*),5(R*),7(R*)-5-|1-hydroxy-1-(2,6-dichlorophenyl)|-methyl-1-methyl-4-phenylpyrrolidin-2-one

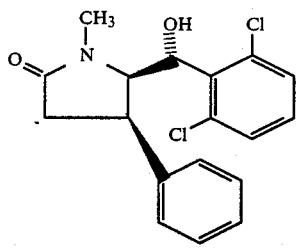

The procedure was analogous to Example 11. 17.85 g (0.079 mol) of 2,6-dichlorobromobenzene and 12.91 g (0.06 mol) of the title compound from Example 5 were used. 4.7 g (22.3% of theory) of the title compound were obtained of melting point: 156° C.

$^1$H-NMR (200 MHz, CDCl$_3$): $\delta = 2.53$ (dd, A-part of ABM system, $J_{AB}=17.5$ Hz, $J_{AM}=9.5$ Hz, 1H, cis-C(3)-H); 2.92 (s, 3H, N-CH$_3$); 3.08 (dd, B-part of ABM system, $J_{BM}=11$ Hz, 1H, trans-C(3)-H); 3.50 (d, J=9 Hz, 1H, OH); 3.80 (dt, M-part of ABM system, $J_{4.5}=7.5$ Hz, 1H, C(4)-H); 4.49 (dd, J=7.5 Hz, J=5 Hz, 1H, C(5)-H); 5.16 (dd, J=9 Hz, J=5 Hz, 1H, C(7)-H); 6.9–7.35 (m, 8H, aromatic H).

EXAMPLE 15

(±)
4(R*),5(R*),7(R*)-5-(1-hydroxy-1-p-fluorophenyl)-methyl-1-methyl-4-phenylpyrrolidin-2-one

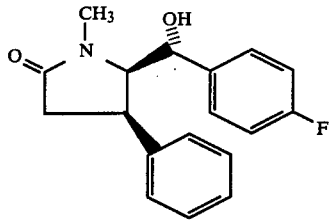

The procedure was analogous to Example 11. 13.83 g (0.079 mol) of 4-fluorobromobenzene and 12.19 g (0.06 mol) of the title compound from Example 5 were used. 10.19 g (61.6% of theory) of the title compound were obtained of melting point: 211°–213° C. and $R_f$ (ethyl acetate)=0.45.

$^1$H-NMR (300 MHz, CDCl$_3$): δ=2.47 (s, 3H, NCH$_3$); 2.49 (dd, A-part of ABM system, $J_{AB}$=15.7 Hz, $J_{AM}$=8.2 Hz, 1H, cis-C(3)-H); 2.55 (broad, 1H, OH); 3.20 (dd, B-part of ABM system, $J_{BM}$=13 Hz, 1H, trans-C(3)-H); 3.82 (dt, M-part of ABM system, $J_{4.5}$=7.5 HZ, 1H, C(4)-H); 4.01 (dd, J=7.5 Hz, J=1 Hz, 1H, C(5)-H); 4.48 (d, J=1 Hz, 1H, C(7)-H); 6.95, 7.15, 7.28 and 7.35 (in each case m, 9H, aromatic H).

EXAMPLE 16

(±)
4(R*),5(R*)-5-(p-chlorobenzoyl)-1-methyl-4-phenyl-pyrrolidin-2-one

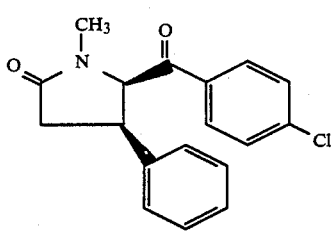

The procedure was analogous to Example 7. 7.9 g (0.025 mol) of the title compound from Example 11 were used. 5.72 g (73.1% of theory) of the title compound were obtained which were processed further without purification.

$^1$H-NMR (200 MHz, CDCl$_3$): δ=2.93 (quint, AB-part of ABM signal, $J_{AB}$=17.5 Hz, $J_{AM}$,$J_{BM}$=9.5 Hz, 2H, C(3)-H); 4.03 (q, M-part of ABM signal, $J_{AM}$=$J_{BM}$=$J_{4.5}$=9.5 Hz, 1H, C(4)-H); 5.39 (d, J=9.5 Hz, 1H, C(5)-H); 7.04 (s, 5H, C$_6$H$_5$); AB signal (δ$_A$=7.2, δ$_B$=7.46, J=Ab=9.5 Hz, 4H, C$_6$H$_4$Cl).

EXAMPLE 17

(±)
4(R*),5(R*)-5-m-fluorobenzoyl-1-methyl-4-phenylpyrrolidin-2-one

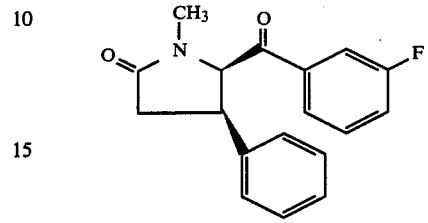

The procedure was analogous to Example 7. 7.48 g (0.025 mol) of the title compound from Example 12 were used. 6.36 g (85.6% of theory) of the title compound were obtained which were processed further without purification.

$^1$H-NMR (200 MHz, CDCl$_3$): δ=2.92 (quint, AB-part of ABM signal, $J_{AB}$=17.5 Hz, $J_{AM}$=$J_{BM}$=9.5 Hz, 2H, (C(3)-H); 4,01 (q, M-part of ABM signal, $J_{AM}$=$J_{BM}$=$J_{4.5}$=9.5 Hz, 1H, C(4)-H); 5.39 (d, J=9.5 Hz, 1H, C(5)-H); 703 (s, 5H, C$_6$H$_5$); 7.05–7.35 (m, 4H, C$_6$H$_4$F).

EXAMPLE 18

(±)
4(R*),5(R*)-5-p-fluorobenzoyl-1-methyl-4-phenyl-pyrrolidin-2-one

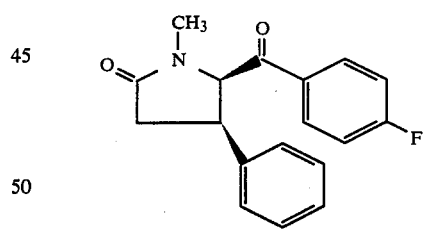

The procedure was analogous to Example 7. 7.28 g (0.016 mol) of the title compound from Example 15 were used. 5.78 g (80% of theory) of the title compound were obtained which were processed further without purification.

$^1$H-NMR (200 MHz, CDCl$_3$): δ=ABM signal (δ$_A$=2.72, δ$_B$=2.89, $J_{AB}$=16 Hz, $J_{AM}$=9.5 Hz, 2H, C(3)-H); 2.88 (s, 3H, NCH$_3$); 3.98 (q, M-part of ABM signal, $J_{BM}$=$J_{4.5}$=9.5 Hz, 1H, C(4)-H); 5.34 (d, J=9.5 Hz, 1H, C(5)-H); 6.87 and 7.5 (in each case m, 4H, C$_6$H$_4$F); 7.0 (s, 5H, C$_6$H$_5$).

EXAMPLE 19

(±)
4(R*),5(R*),7(S*)-5-(1-hydroxy-1-m-flourophenyl)-methyl-1-methyl-4-phenylpyrrolidin-2-one

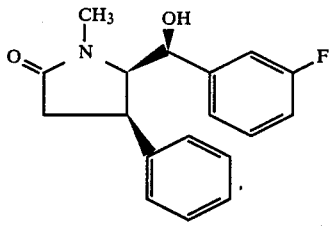

5.95 g (0.02 mol) of the title compound from Example 17 were dissolved in 98 ml of absolute methanol, mixed with 0.77 g (0.02 mol) of sodium borohydride and heated to 60° C. until starting material was no longer present in the TLC (2-3 h). The product was poured onto 200 ml of phosphate buffer solution (pH=4), the reaction product was filtered off with suction and rinsed well with water. After drying in high vacuum, 4.92 g (82.2 of theory) of the title compound were obtained which were further reacted directly.

$^1$H-NMR (200 MHz, CDCl$_3$/DMSO): δ=2.18 and 2.38 (AMB signal, $J_{AB}$=16 Hz, $J_{AM}$=9 Hz, $J_{BM}$=12.5 Hz, 2H, C(3)-H); 3.04 (s, 3H, N-CH$_3$); 3.82 (dt, M-part of ABM signal, $J_{4,5}$=9 Hz, 1H, C(4)-H); 4.24 (dd, J=9 Hz, J=2 Hz, 1H, C(5)-H); 4.77 (dd, J=2 Hz, J=4 Hz, 1H, C(7)-H); 5.19 (d, J=4 Hz, 1H, OH); 6.37 (d, J=10 Hz, 1H, from C$_6$H$_4$F); 6.55 (d, J=7.5 Hz, 1H, from C$_6$H$_4$F); 6.75, 7.07 and 7.18 (in each case m, C$_6$H$_5$ and C$_6$H$_4$F).

EXAMPLE 20

(±)
4(R*),5(R*),7(S*)-5-(1-hydroxy-1-m-chlorophenyl)-methyl-1-methyl-4-phenylpyrrolidin-2-one

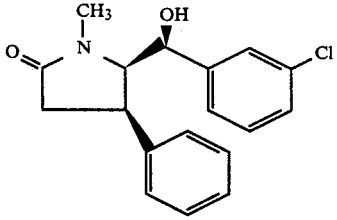

The procedure was analogous to Example 19. 5.17 g (0.0164 mol) of (±) 4(R*),5(R*)-5-(3-chloro)benzoyl-1-methyl-4-phenylpyrrolidin-2-one) (prepared analogously to Example 7) were used. 4.79 g (92.4% of theory) of the title compound were obtained.

$^1$H-NMR (200 MHz, CDCl$_3$/DMSO): δ=2.15 and 2.45 (A and B-part of ABM signal, $J_{AB}$=16 Hz, $J_{AM}$=9 Hz, $J_{BM}$=12.5 Hz, 2H, C(3)-H); 3.0 (S, 3H, N-CH$_3$); 3.81 (dt, $J_{4,5}$=8 Hz, 1H, C(4)-H); 4.26 (dd, J=8 Hz, J=2.5 Hz, 1H, C(5)-H); 4.75 (dd, J=2.5 Hz, J=4.5 Hz, 1H, C(7)-H); 6.56 (s, 1H, C(2)-C$_6$H$_4$Cl); 6.70, 7.05 and 7.15 (in each case m, 8H, C$_6$H$_5$ and C$_6$H$_3$Cl).

EXAMPLE 21

(±)
4(R*),5(R*),7(S*)-5-(1-hydroxy-1-p-chlorophenyl)-methyl-1-methyl-4-phenylpyrrolindin-2-one

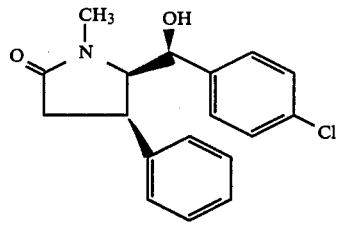

The procedure was analogous to Example 19. 5.45 g (0.02 mol) of the title compound from Example 16 were used. 5.47 g (99% of theory) of the title compound were obtained.

$^1$H-NMR (200 MHz, CDCl$_3$/DMSO): δ=2.15 (d, J=10 Hz, 2H, C(3)-H); 3.06 (s, 3H, N-CH$_3$); 3.82 8q, broad, J=10 Hz, 1H, C(4)-H); 4.26 (dd, J=8 Hz, J=2.5 Hz, 1H, C(5)-H); 4.72 (dd, J=2.5 Hz, J=4.5 Hz, 1H, C(7)-H); 5.25 (d, J=4.5 Hz, 1H, OH); 6.64 (d, J=9 Hz, 2H, AB signal of C$_6$H$_4$Cl); 7.04 (d, J=9 Hz, 2H, AB signal of C$_6$H$_4$Cl); 7.06 and 7.20 (in each case m, 5H, C$_6$H$_5$).

EXAMPLE 22

(±)
3(S*),4(R*),5(R*),7(S*)-3-hydroxy-5(1-hydroxy-1m-flourophenyl)methyl-1-methyl-4-phenlpyrrolidin-2-one

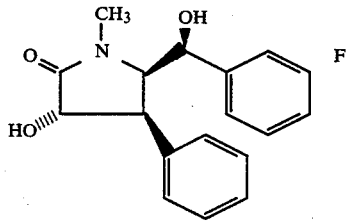

The proceducer was analogous to Example 9. 2 g (0.0067 mol) of the title compound from Example 19 were used. After chromatography (see Example 19) 0.61 g (31% of theory) of the pure title compound was obtained.

Retention time: 6.07 min (HPLC, Hibar prepack column 250-4, Lichrosorb Si 60 (5 μm), eluent: ethyl acetate/MeOH=20/1; 1 ml/min). It was possible to recover 0.7 g (35% of theory) of the starting compound.

$^1$H-NMR (200 MHz, CDCl$_3$/DMSO): δ=3.16 (s, 3H, N-CH$_3$); 3.64 (dd, J=10.5 Hz, J=7.5 Hz, 1H, C(4)-H); 4.13 (dd, J=5.5 Hz, J=10.5 Hz, 1H, C(3)-H); 4.26 (dd, J=7.5 Hz, J=1 Hz, 1H, C(5)-H); 4.83 (dd, J=1 Hz, J=4 Hz, 1H, C(7)-H); 5.23 (d, J=5.5 Hz, 1H, C(3)-OH, exchangeable with D$_2$O); 5.38 (d, J=4 Hz, 1H, C(7)-OH, exhangeable with D$_2$O); 6.40 (d, J=10 Hz, 1H, from C$_6$H$_4$F); 6.58 (d, J=7.5 Hz, 1H from C$_6$H$_4$F); 6.80 and 7.13 (in each case m 7H, C$_6$H$_5$ and from C$_6$H$_4$F).

EXAMPLE 23

(±)
3(S*),4(R*),5(R*),7(S*)-3-hydroxy-5-1-hydroxy-(p-chlorophenyl)-methyl-1-methyl-4-phenylpyrrolidin-2-one

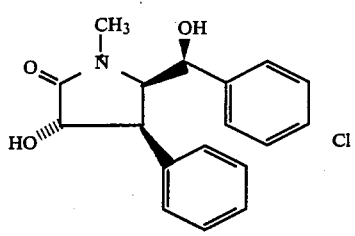

The procedure was analogous to Example 9. 2.0 g (0.0063 mol) of the title compound from Example 21 were used. 0.71 g (31% of theory) of the pure title compound was obtained with a retention time of 6.34 min (see Example 22 for conditions) and melting point 254°–7° C. It was possible to recover 0.3 g of the starting material unchanged.

$^1$H-NMR (300 MHz, CDCl$_3$/DMSO): δ=3.11 (s, 3H, N-CH$_3$); 3.58 (dd, J=7.5 Hz, J=10.5 Hz, 1H, C(4)-H); 3.90 (dd, J=10.5 Hz, J=5.5 Hz, 1H, C(3)-H); 4.20 (dd, J=7.5 Hz, J=2 Hz, 1H, C(5)-H); 4.50 (d, J=5.5 Hz, 1H, C(3)-OH, exchangeable with D$_2$O); 4.70 (t, J=2 Hz, 1H, C(7)-H); 4.80 (d, J=2 Hz, 1H, C(7)-OH, exchangeable with D$_2$O); 6.58 and 6.98 (AB signal, J$_{AB}$=8.3 Hz, 4H, C$_6$H$_4$Cl); 7.13 (m, 5H, C$_6$H$_5$).

It will be appreciated that the instant specification and claims are set forth by way of illustration and not limitation, and that various modifications and changes may be made without departing from the spirit and scope of the present invention.

What is claimed is:

1. A process for the preparation of a C(3)–C(4)-transconfigurated γ-butyrolactam of the general formula (I)

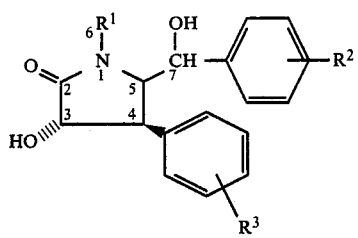

in which
R$^1$ represents hydrogen or alkyl, aryl or aralkyl with in each case up to 10 carbon atoms and
R$^2$ and R$^3$ are identical or different and represent hydrogen, alkyl, alkoxy, with in each case up to 10 carbon atoms, phenyl, benzyl, phenoxy, benzloxy, benzoyl, acetyl, trifluoromethyl, trifluoromethoxy, nitro, hydroxy, halogen, amino, carboxyl, sulpho, dialkylamino with up to 4 carbon atoms in the alkyl groups or acylamino with up to 18 carbon atoms, and isomers, isomer mixtures, racemates or optical antipodes of said δ-butyrolactam, comprising reacting a starting compound of the formula (II)

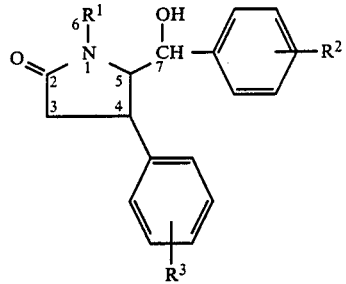

in which
R$^1$, R$^2$ and R$^3$ have the above-mentioned meanings with an oxidizing agent selected from the group consisting of peroxoacetic acid, chloroperbenzoic acid, molybdenum peroxide/pyridine complex, oxygen, ozone and 2-sulphonyloxaziridine in an inert organic solvent in the presence of a base selected from the group consisting of an alkali metal alcoholate, an alkali metal amide, an alkali metal hydride, an organo-alkali metal compound, 1,5-diazabicyclo(4,3,0)non-5-ene and 1,8-diazabicyclo(5,4,0)undec-7-ene and further in the presence of a phosphite auxiliary, wherein the reaction is conducted at a temperature of −100° C. to +20° C., and wherein 1 to 5 moles of base are employed per mole of starting compound.

2. A process according to claim 1, wherein said alkyl and alkoxy have up to 6 carbon atoms.

3. A process according to claim 1, wherein
R$^1$ represents alkyl with up to 4 carbon atoms and
R$^2$ and R$^3$ are identical or different and represent alkyl with up to 4 carbon atoms, alkoxy with up to 4 carbon atoms, phenyl, benzyl, phenoxy, benzyloxy, benzoyl, acetyl, trifluoromethyl, triflouromethoxy, nitro, flourine, chlorine, bromine, hydroxyl, amino, dimethylamino, diethylamino, acetylamino, carboxyl or sulpho.

4. A process according to claim 1, wherein the compound of formula (II) is (±)4(S*),5(R*),7(S*)-5-α-hydroxy-benzyl-1-methyl-4-phenylpyrroldin-2-one.

5. A process according to claim 1, wherein the base is a tertiary amine suitable for enolate formation.

6. A process according to claim 1, wherein the auxiliary is a phosphite.

7. A process according to claim 6, wherein the oxidizing agent is oxygen, wherein the solvent is selected from the group consisting of tetrahydrofuran, hexamethylphosphoric acid triamide and mixtures thereof, and wherein the auxiliary is triethyl phosphite.

8. A process according to claim 1, wherein 1 to 2.5 moles of base are employed per mole of starting compound.

9. A process according to claim 1, wherein the 0.5 to 5 moles of auxiliary are employed per mole of starting compound.

10. A process according to claim 1, wherein the base is selected from the group consisting of an alkali metal alcoholate, an alkali metal amide, an alkali metal hydride, an organo-alkali metal compound and a tertiary amine.

11. A process according to claim 1, wherein the phosphite auxiliary is selected from the group consisting of trimethyl phosphite, triethyl phosphite, tripropyl phosphite, triisopropyl phosphite, tributyl phosphite and triphenyl phosphite.

12. A process according to claim 1, wherein the base is selected from the group consisting of sodium methanolate, potassium methanolate, sodium ethanolate, potassium ethanolate, potassium tert.-butanolate, sodium hydride, sodium amide, lithium diisopropylamide, butyl-lithium, phenyl-lithium and lithium hexamethylpiperidide.

13. A process according to claim 1, wherein the process is conducted at normal pressure.

* * * * *